US006496737B2

(12) United States Patent
Rudie et al.

(10) Patent No.: US 6,496,737 B2
(45) Date of Patent: Dec. 17, 2002

(54) THERMAL THERAPY CATHETER

(75) Inventors: Eric N. Rudie, Maple Grove, MN (US); Scott Stockmoe, Maple Grove, MN (US); Aaron Hjelle, Champlin, MN (US); Bruce W. Ebner, Shorewood, MN (US); Joel Crabb, Minneapolis, MN (US); Jonathan L. Flachman, Robbinsdale, MN (US); Stan Kluge, Watertown, MN (US); Satish Ramadhyani, Minneapolis, MN (US); Bruce Neilson, Brooklyn Park, MN (US)

(73) Assignee: Urologix, Inc., Minneapolis, MN (US)

( * ) Notice: Subject to any disclaimer, the term of this patent is extended or adjusted under 35 U.S.C. 154(b) by 26 days.

(21) Appl. No.: 09/733,109

(22) Filed: Dec. 8, 2000

(65) Prior Publication Data

US 2001/0016761 A1 Aug. 23, 2001

Related U.S. Application Data

(63) Continuation-in-part of application No. 09/303,259, filed on Apr. 30, 1999, now Pat. No. 6,161,049.
(60) Provisional application No. 60/126,330, filed on Mar. 26, 1999.

(51) Int. Cl.$^7$ .................................................. A61F 2/00
(52) U.S. Cl. ........................ 607/101; 607/102; 607/105
(58) Field of Search ............................. 606/28, 29, 31; 607/101, 102, 96, 104, 105, 113

(56) References Cited

U.S. PATENT DOCUMENTS

| 4,342,316 A | 8/1982 | Rosenberg |
| 4,406,656 A | 9/1983 | Hattler et al. |
| 4,643,186 A * | 2/1987 | Rosen et al. ................. 606/159 |
| 4,662,383 A | 5/1987 | Sogawa et al. |
| 4,676,258 A | 6/1987 | Inokuchi et al. |
| 4,825,880 A * | 5/1989 | Stauffer et al. ............. 607/156 |
| 4,878,495 A | 11/1989 | Grayzel |
| 4,887,614 A | 12/1989 | Shirakami et al. |
| 4,983,165 A | 1/1991 | Loiterman |
| 5,007,437 A | 4/1991 | Sterzer |
| 5,015,231 A | 5/1991 | Keith et al. |
| 5,108,370 A * | 4/1992 | Walinsky ............... 604/102.02 |
| 5,195,965 A | 3/1993 | Shantha |

(List continued on next page.)

FOREIGN PATENT DOCUMENTS

JP            4-28377            1/1992

Primary Examiner—Roy D. Gibson
(74) Attorney, Agent, or Firm—Kinney & Lange, P.A.

(57) ABSTRACT

A thermal therapy catheter includes a catheter shaft having an outer surface that is insertable into the body lumen. The catheter shaft carries an energy-emitting element. A multi-lobe balloon is positioned around the outer surface of the catheter shaft adjacent to the energy-emitting element, with opposing ends of the multi-lobe balloon being sealingly connected to the catheter shaft to form a chamber between the multi-lobe balloon and the outer surface of the catheter shaft. Fluid is circulated between the outer surface of the catheter shaft and the multi-lobe balloon in a defined fluid flow path to firmly contact the wall of the body lumen and thereby cool the body lumen tissue while thermally treating targeted tissue at a depth from the body lumen wall.

20 Claims, 10 Drawing Sheets

U.S. PATENT DOCUMENTS

| | | |
|---|---|---|
| 5,226,887 A | 7/1993 | Farr et al. |
| 5,304,214 A | 4/1994 | DeFord et al. |
| 5,308,323 A | 5/1994 | Sogawa et al. |
| 5,308,356 A | 5/1994 | Blackshear, Jr. et al. |
| 5,350,361 A | 9/1994 | Tsukashima et al. |
| 5,383,856 A | 1/1995 | Bersin |
| 5,496,271 A | 3/1996 | Burton et al. |
| 5,501,667 A | 3/1996 | Verduin, Jr. |
| 5,505,702 A | 4/1996 | Arney |
| 5,549,559 A | 8/1996 | Eshel |
| 5,645,529 A | 7/1997 | Fagan et al. |
| 5,800,486 A | 9/1998 | Thome et al. |
| 5,843,144 A | 12/1998 | Rudie et al. |
| 5,861,021 A | 1/1999 | Thome et al. |
| 5,899,932 A | 5/1999 | Dann et al. |
| 5,916,240 A | 6/1999 | Rudie et al. |
| 5,931,860 A | 8/1999 | Reid et al. |
| 5,938,692 A | 8/1999 | Rudie |
| 5,987,360 A | 11/1999 | McGrath et al. |
| 5,992,419 A | 11/1999 | Sterzer et al. |
| 6,002,968 A * | 12/1999 | Edwards ............ 606/41 |
| 6,007,571 A | 12/1999 | Neilson et al. |
| 6,009,351 A | 12/1999 | Flachman |
| 6,096,030 A * | 8/2000 | Ortiz ............ 606/14 |
| 6,122,551 A | 9/2000 | Rudie et al. |

* cited by examiner

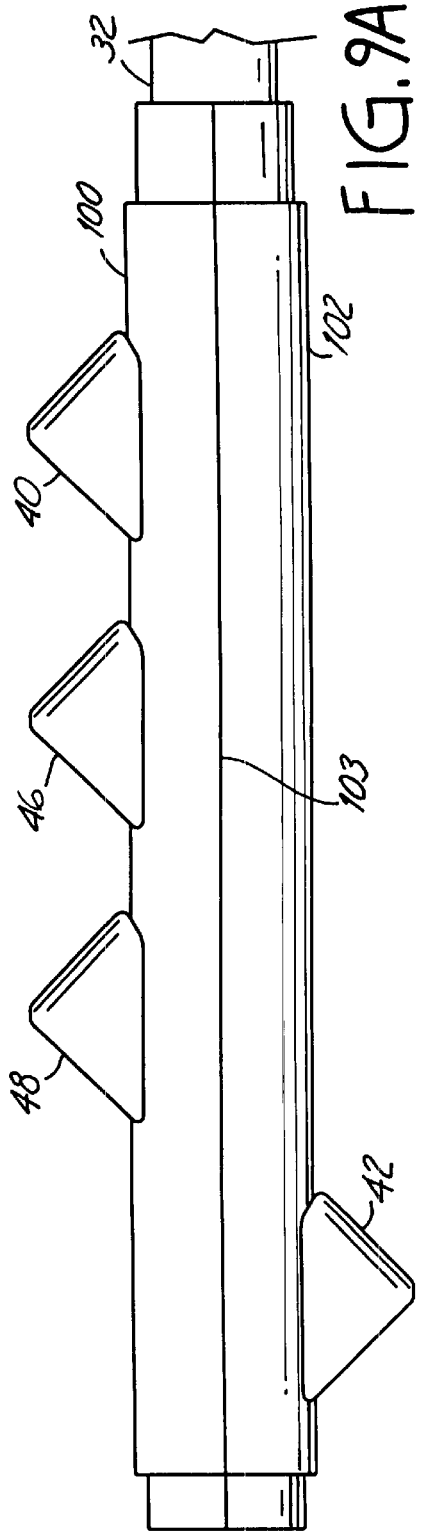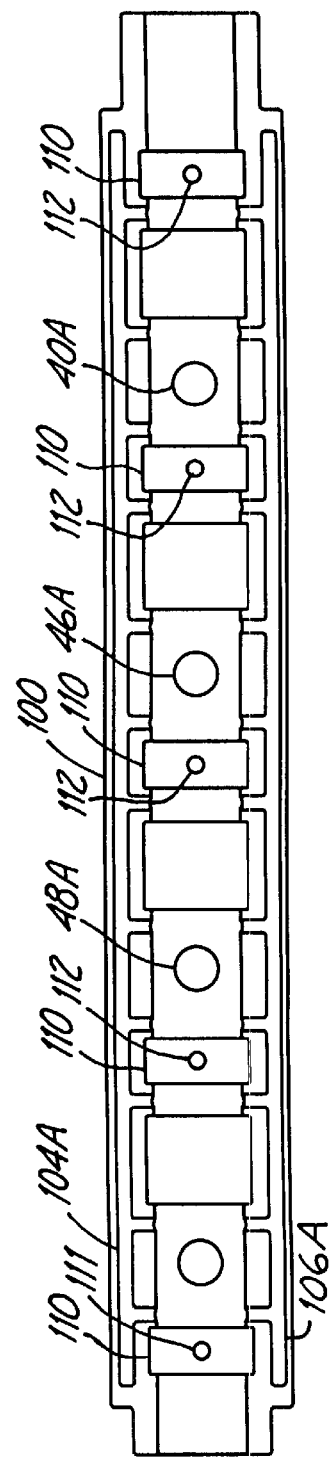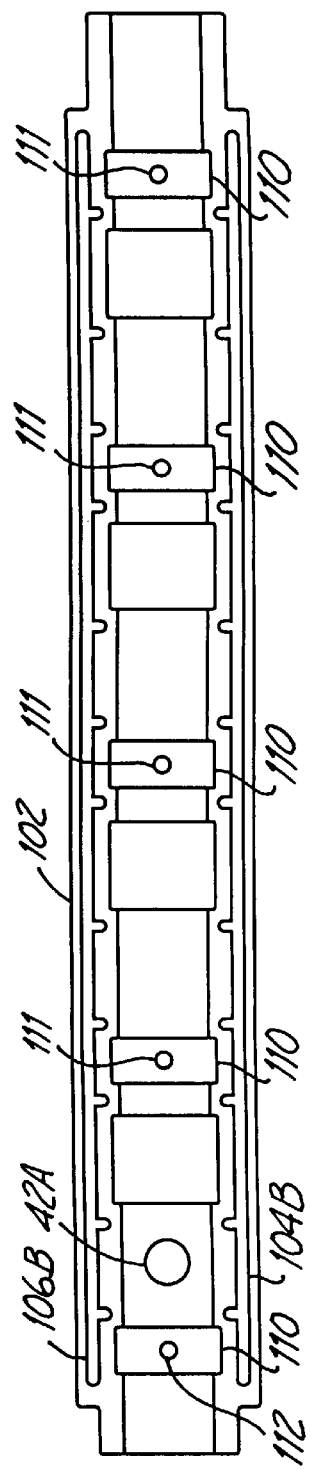

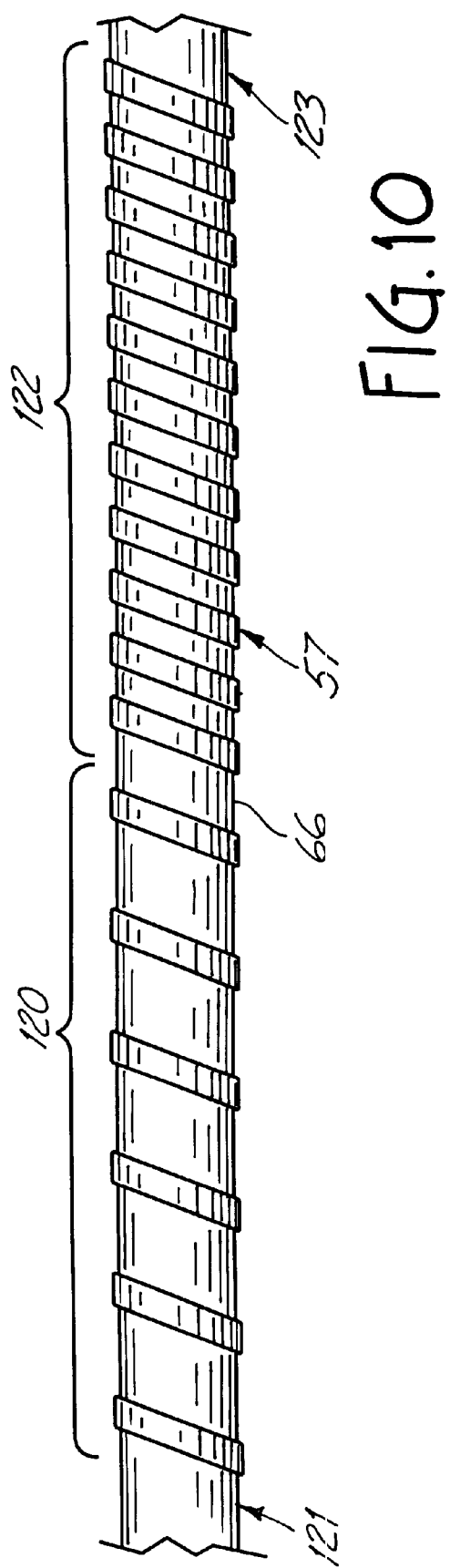

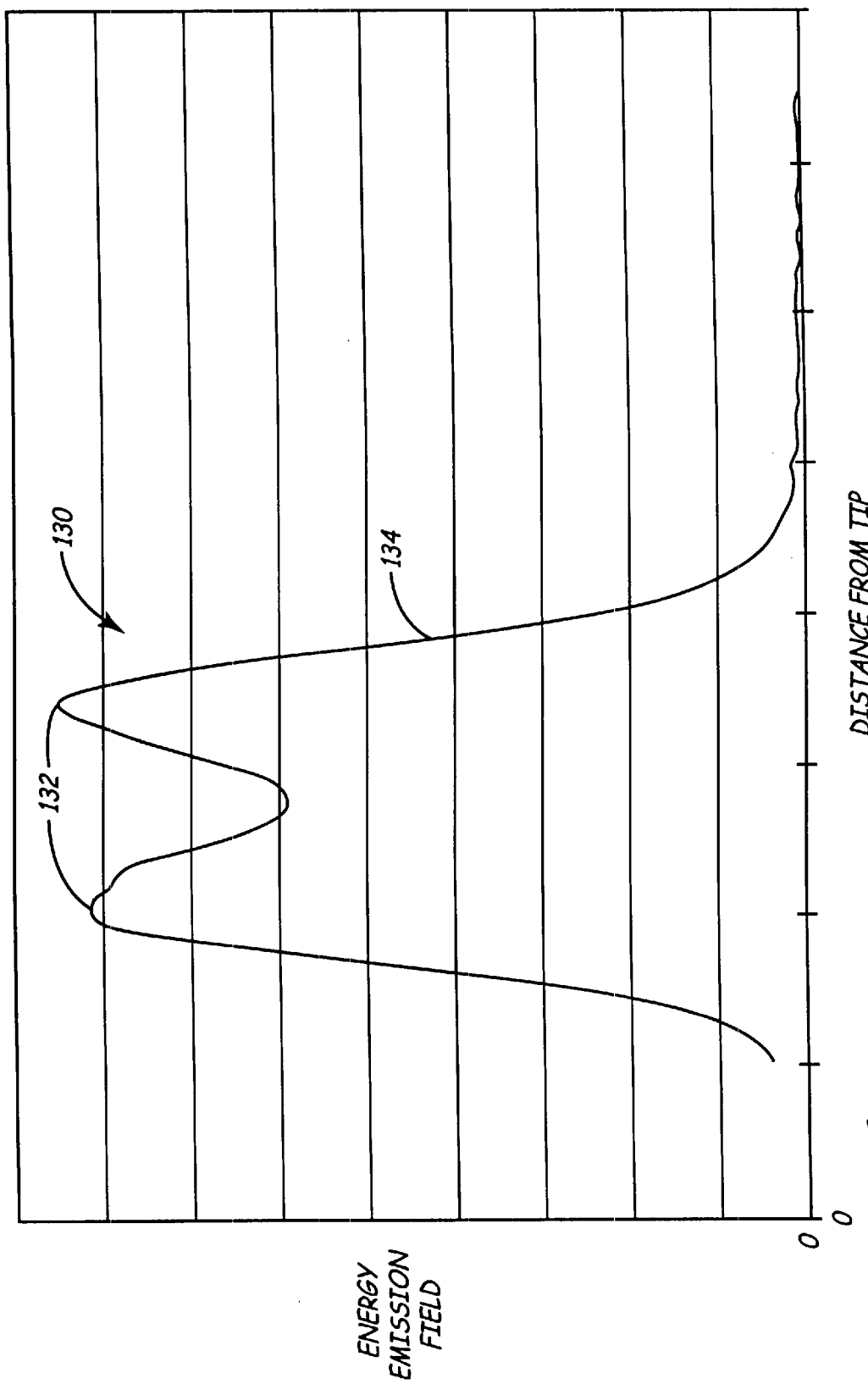

THERMAL THERAPY CATHETER

CROSS-REFERENCE TO RELATED APPLICATION(S)

This application is a continuation-in-part of U.S. application Ser. No. 09/303,259 filed Apr. 30, 1999 U.S. Pat. No. 6,161,049 for "Thermal Therapy Catheter" by E. Rudie, S. Stockmoe, A. Hjelle, B. Ebner and J. Crabb, which in turn claims priority from Provisional Application No. 60/126,330 filed Mar. 26, 1999 for "Thin-Walled Catheter Having Defined Fluid Flow Path" by E. Rudie, S. Stockmoe and A. Hjelle.

INCORPORATION BY REFERENCE

The aforementioned U.S. application Ser. No. 09/303,259 is hereby incorporated by reference in its entirety.

BACKGROUND OF THE INVENTION

The present invention relates to a thermal treatment catheter, and more particularly to a catheter having a thin outer wall and a defined fluid flow path within the outer wall to improve the effects of conductive cooling of the wall of the body conduit in which the catheter is inserted.

The prostate gland is a complex, chestnut-shaped organ which encircles the urethra immediately below the bladder. Nearly one third of the prostate tissue anterior to the urethra consists of fibromuscular tissue that is anatomically and functionally related to the urethra and the bladder. The remaining two thirds of the prostate is generally posterior to the urethra and is comprised of glandular tissue. The portion of the urethra extending through the prostate (i.e., the prostatic urethra) includes a proximal segment, which communicates with the bladder, and a distal segment, which extends at an angle relative to the proximal segment by the verumontanum.

Although a relatively small organ, the prostate is the most frequently diseased of all internal organs and is often the site of a common affliction among older men, benign prostatic hyperplasia (BPH), as well as a more serious affliction, cancer. BPH is a nonmalignant, bilateral expansion of prostate tissue occurring mainly in the transition zone of the prostate adjacent to the proximal segment of the prostatic urethra. As this tissue grows in volume, it encroaches on the urethra extending into the region of the bladder neck at the base of the bladder. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Benign prostatic hyperplasia (BPH) may be treated using transurethral thermal therapy as described in further detail in U.S. Pat. No. 5,413,588 entitled DEVICE AND METHOD FOR ASYMMETRICAL THERMAL THERAPY WITH HELICAL DIPOLE MICROWAVE ANTENNA and in U.S. Pat. No. 5,575,811 entitled BENIGN PROSTATIC HYPERPLASIA TREATMENT CATHETER WITH URETHRAL COOLING, both of which are hereby incorporated by reference. During transurethral thermal therapy, the transition zone of the prostate is heated to necrose the tumorous tissue that encroaches on the urethra. Transurethral thermal therapy is administered by use of a microwave antenna-containing catheter which includes a multi-lumen shaft. The catheter is positioned in the urethra with the microwave antenna located adjacent to the hyperplastic prostatic tissue. Energization of the microwave antenna causes the antenna to emit electromagnetic energy which heats tissue within the prostate. A cooling fluid is circulated through the catheter to preserve tissue such as the urethral wall between the microwave antenna and the target tissue of the prostate.

The commercially available Targis™ system from Urologix, Inc. of Minneapolis, MN employs a thermal therapy catheter that embodies the aforementioned U.S. Pat. No. 5,413,588, and is a product capable of performing thermal therapy of the prostate with microwave energy delivered from an applicator positioned in the urethra. The TargiST system has achieved substantial clinical and commercial success, indicating the efficacy of microwave thermal therapy for treating prostate disease. This therapy is benefitted by further developments in the technology of thermal therapy catheters to enhance the effects of microwave treatment of the prostate.

BRIEF SUMMARY OF THE INVENTION

The present invention is a device and method for treating tissue adjacent to a body lumen such as a urethra. A catheter shaft having an outer surface is insertable into the body lumen, and the catheter shaft carries an energy-emitting element. A multi-lobe balloon is positioned around the outer surface of the catheter shaft adjacent to the energy-emitting element, with opposing ends of the multi-lobe balloon being sealingly connected to the catheter shaft to form a chamber between the multi-lobe balloon and the outer surface of the catheter shaft. Fluid is circulated between the outer surface of the catheter shaft and the multi-lobe balloon in a defined fluid flow path to firmly contact the wall of the body lumen and thereby cool the body lumen tissue while thermally treating targeted tissue at a depth from the body lumen wall.

BRIEF DESCRIPTION OF THE DRAWINGS

FIG. 9 is a diagram illustrating the handle of the thermal therapy catheter of the present invention.

FIG. 10 is a diagram illustrating an antenna configuration used in one embodiment of the present invention.

FIG. 11 is a graph illustrating the effects of the antenna configuration shown in FIG. 10.

DETAILED DESCRIPTION

Figure 1:
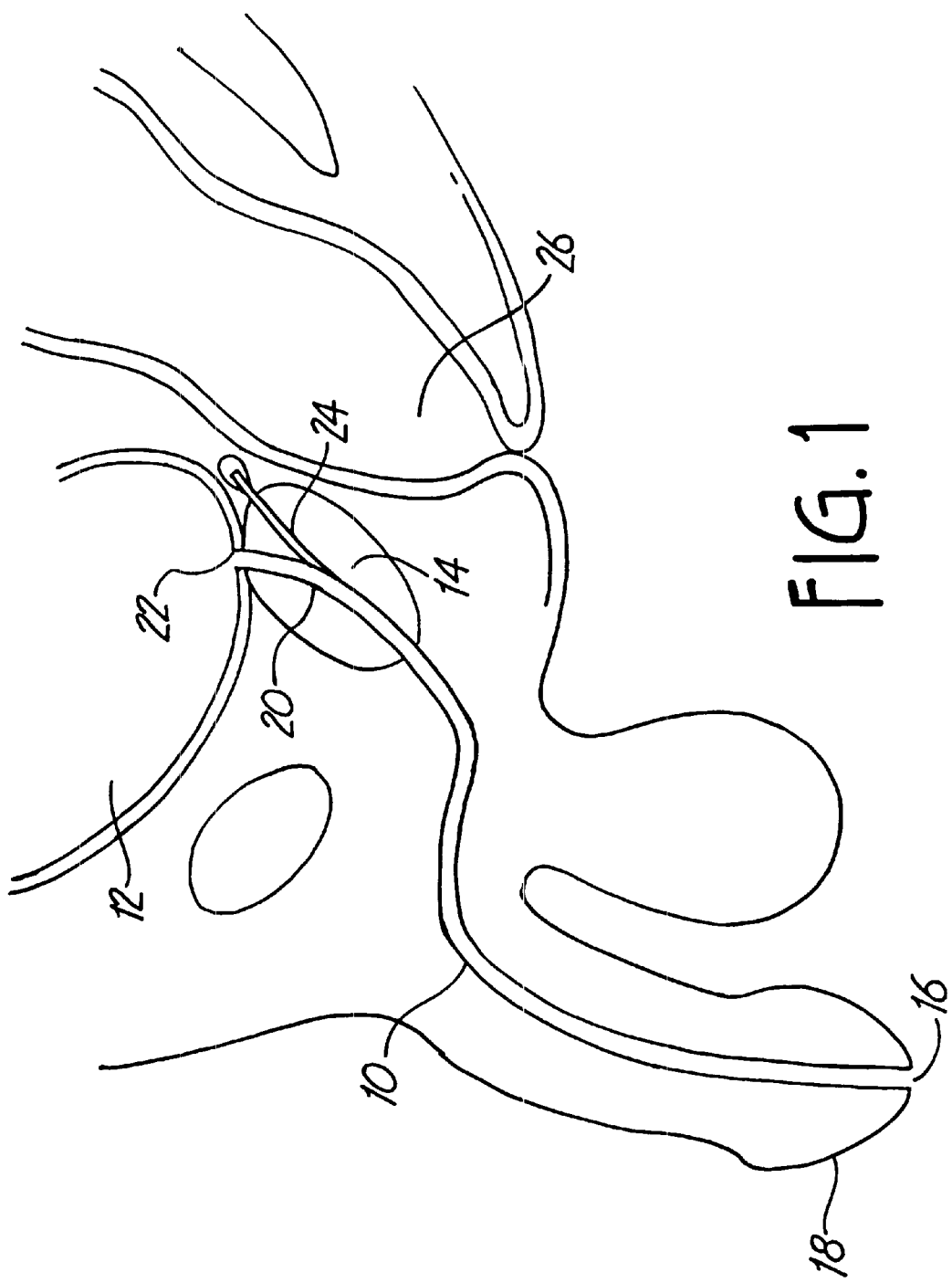
FIG. 1 is a vertical sectional view of a male pelvic region showing the urinary organs affected by benign prostatic hyperplasia.

FIG. 1 is a vertical sectional view of a male pelvic region showing the effect benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, with the present invention, a selected volume of tissue of prostate 14 can be necrosed while preserving the tissue of urethra 10 and adjacent tissue such as ejaculatory duct 24 and rectum 26. This is achieved by microwave antenna-carrying catheter 28 of the present invention, which is shown in FIGS. 2–10.

Catheter System

Figure 2:
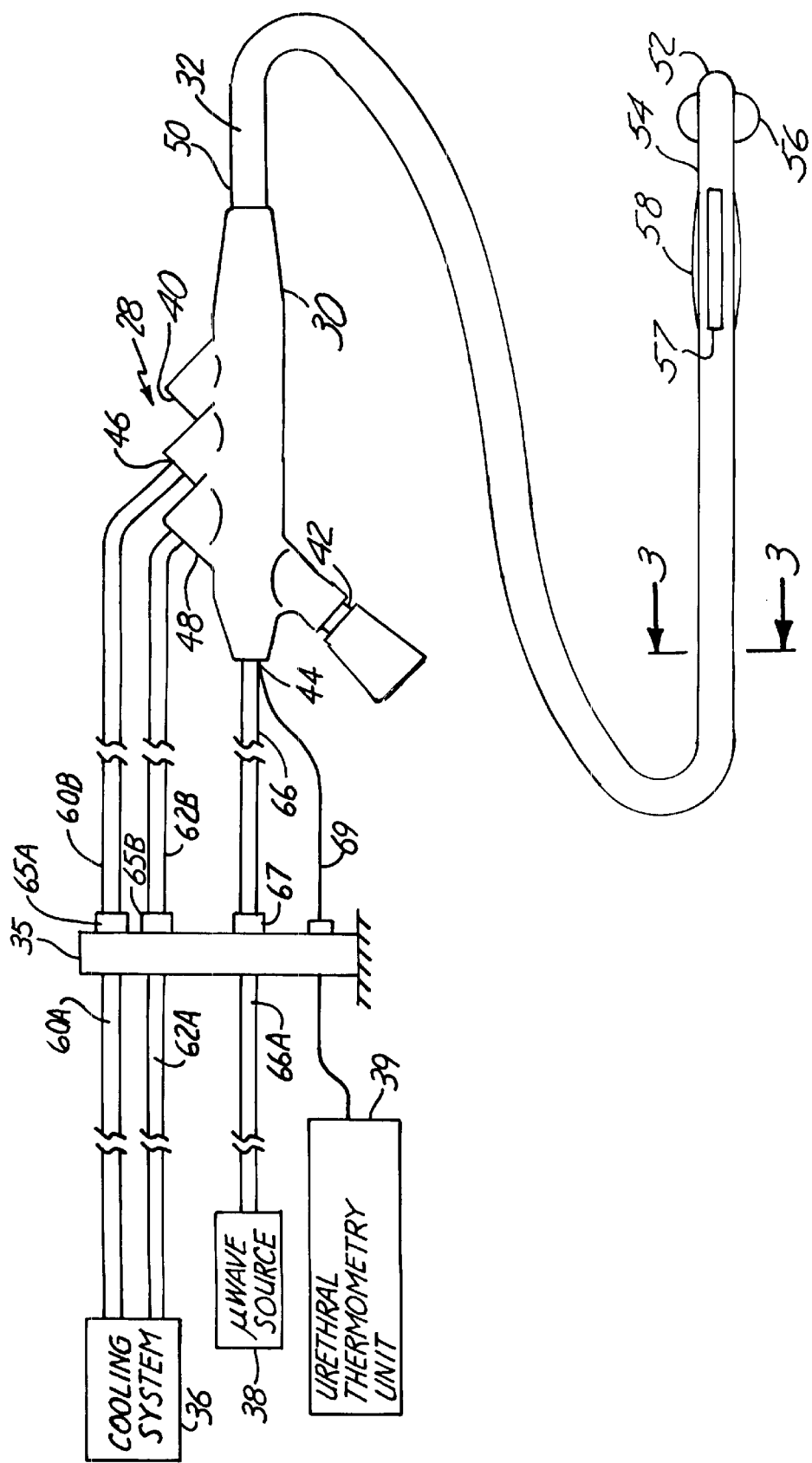
FIG. 2 is a diagram illustrating the thermal therapy catheter of the present invention.

FIG. 2 is a diagram illustrating a thermal therapy catheter system of the present invention. This system comprises catheter 28 and generally includes multi-port handle 30, multi-lumen shaft 32, connection manifold 35, cooling system 36, microwave generating source 38 and thermometry unit 39. Multi-port handle 30 includes inflation port 40, urine drainage port 42, microwave antenna port 44 (which also receives a temperature sensing fiber), cooling fluid intake port 46 and cooling fluid exit port 48. Ports 40–48 communicate with corresponding lumens within shaft 32. Handle 30 is preferably constructed as a two-piece snap-fit shell, composed of a thermoplastic elastomer or a similar material.

Shaft 32 is connected to handle 30 at shaft proximal end 50, and extends to tip 52 at distal end 54. Shaft 32 is a multi-lumen, Foley-type urethral catheter, with inflatable retention balloon 56 at distal end 54. Shaft 32, which has an outer diameter of about 18 French (6 millimeters (mm)), is generally circular in cross-section, and is both long enough and flexible enough to permit insertion of proximal shaft end 54 through urethra 10 into bladder 12 (FIG. 1), where retention balloon 56 is inflated and seated against the bladder neck to secure the catheter in place. This enables precise. location of microwave antenna 57 with respect to prostate tissue. In a preferred embodiment, catheter shaft 32 is extruded from a thermoplastic elastomer. Thermoplastic materials are less expensive than medicalgrade silicone, and are capable of being thermally processed, thereby obviating the need for adhesive bonding to the silicone, and the relatively long curing times associated therewith.

Multi-lobe balloon 58 is attached to the outer surface of shaft 32 near distal end 54, preferably by thermal welding or a comparable attachment technique such as adhesive bonding, at one or more points on the outer surface of shaft 32 around antenna 57. Multi-lobe balloon 58 is preferably formed of a thermoplastic film wrapped around shaft 32, such as a cross-linked polyurethane blown film in an exemplary embodiment. The construction and operation of multilobe balloon 58 is described in more detail below.

Cooling system 36 provides cooling fluid in feed line 60A, which is coupled through manifold 35 to feed line 60B and on through port 46 of handle 30 for communication with an interior lumen of catheter shaft 32. The cooling fluid returns from the interior of catheter shaft 32 through port 48 of handle 30, into return line 62B through manifold 35 to return line 62A and back to cooling system 36 for re-chilling and recirculation. Cooling fluid feed line 60B and return line 62B are provided with conventional fittings 65A and 65B, respectively, which permits catheter 28 to be easily disconnected from cooling system 36. In an exemplary embodiment, the cooling fluid is deionized or sterile water, chilled to an appropriate temperature for effective tissue cooling in operation of catheter 28.

Microwave generating source 38 provides microwave energy to connection cable 66A, which is coupled through manifold 35 to coaxial cable 66. Coaxial cable 66 is provided with conventional connector 67 to permit coaxial cable 66 to be easily disconnected from microwave source 38. Coaxial cable 66 extends through port 44 of handle 30 into an internal lumen of catheter shaft 32 that extends to distal end 54. In an exemplary embodiment, microwave generating source 38 produces up to about 100 watts of electrical power in a frequency range of 902–928 MHz, within the FCC-ISM standard range of frequencies.

Urethral thermometry unit 39 is operatively connected to temperature sensing fiber 69, which extends through manifold 35 into port 44 of handle 30 and on to an internal lumen of catheter shaft 32 that extends to distal end 54. Signals representative of urethral temperature are communicated via temperature sensing fiber 69 and are interpreted and processed by urethral thermometry unit 39. In an exemplary embodiment, temperature sensing fiber 69 is encased in a Kevlar tube, attached to fiber 69 with sufficient slack between tip 52 and handle 30 so that pulling on the exposed portion of the tube outside handle 30 will not break fiber 69.

Figure 3:
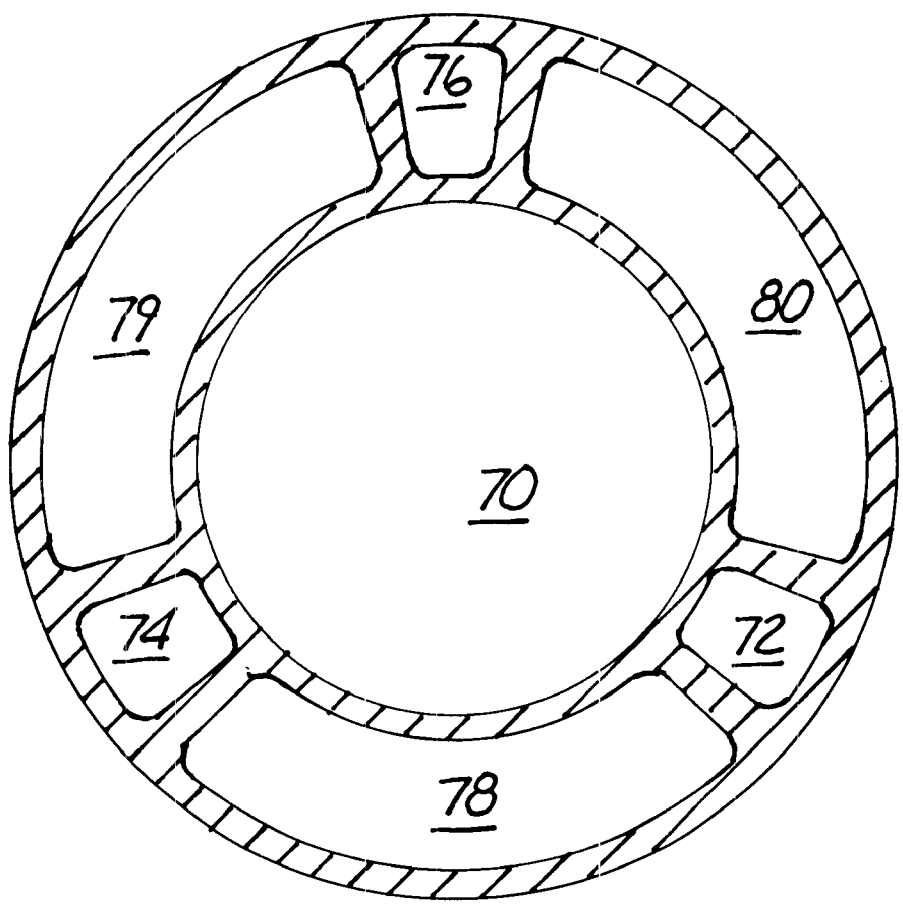
FIG. 3 is a cross-sectional view of the thermal therapy catheter of the present invention, taken along line 3—3 of FIG. 2.
Figure 4:
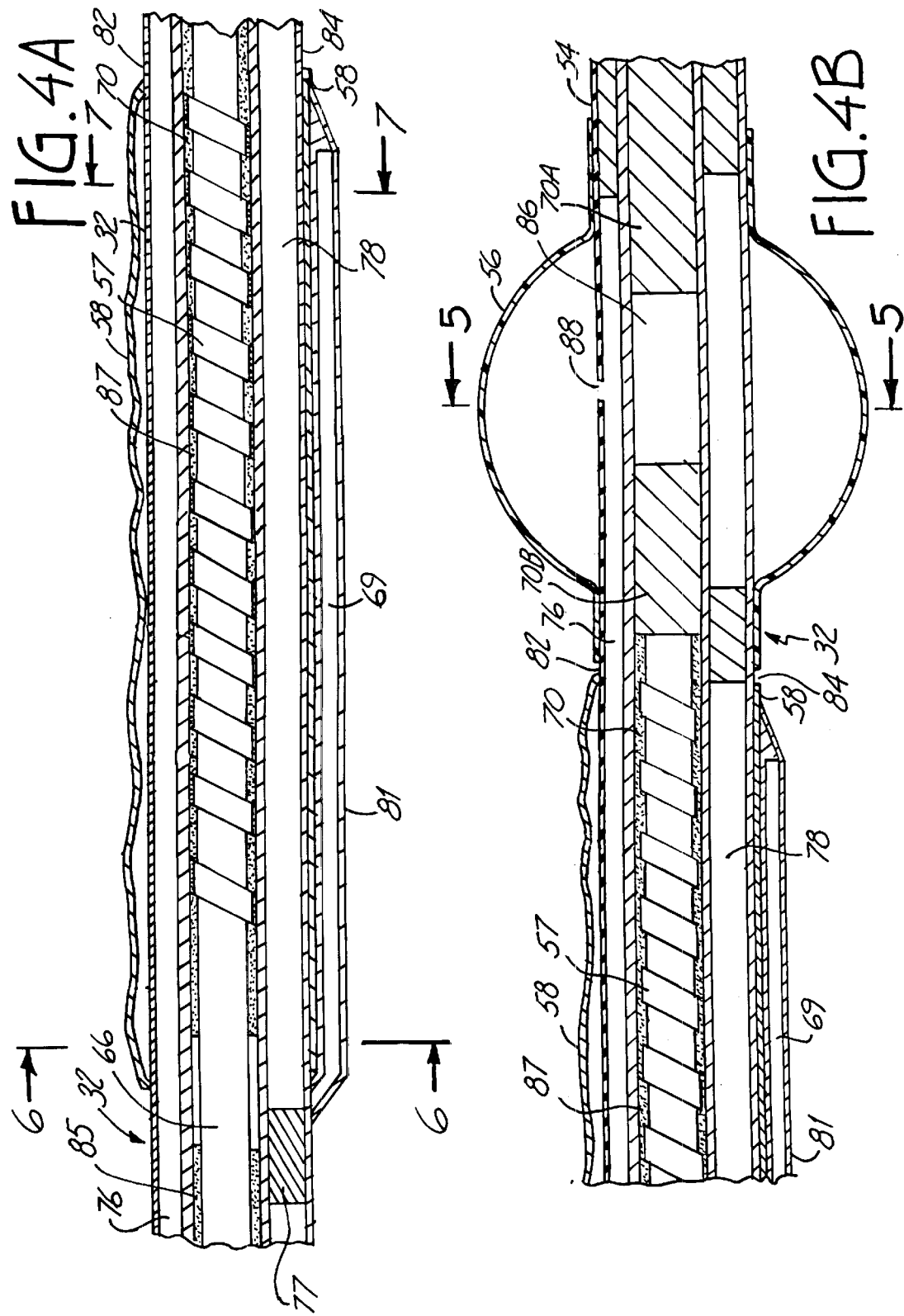
FIG. 4A is a cross-sectional view of a portion of the thermal therapy catheter of the present invention in the vicinity of a multi-lobe balloon and microwave antenna.
FIG. 4B is a cross-sectional view of a portion of the thermal therapy catheter of the present invention in the vicinity of a retention balloon.

FIG. 3 is a sectional view of catheter shaft 32 taken along line 3—3 of FIG. 2, for illustration of the interior lumens of shaft 32. Shaft 32 includes antenna lumen 70, temperature sensing fiber lumen 72, urine drainage lumen 74, balloon inflation lumen 76, and cooling lumens 78, 79 and 80. Lumens 70, 72, 74, 76, 78, 79 and 80 generally extend from proximal shaft end 50 to distal shaft end 54, and are formed by walls within catheter shaft 32 that have a substantially uniform thickness throughout the cross-section of shaft 32, the catheter wall thickness being about 0.008 inches in an exemplary embodiment. Although coaxial cable 66 is contained in antenna lumen 70, it is omitted from FIG. 2 in order to more clearly show the relationships between the interior lumens of catheter shaft 32.

FIGS. 4A and 4B are cross-sectional views of catheter shaft 32 in a region including multi-lobe balloon 58 and retention balloon 56, respectively. Coaxial cable 66 is positioned within antenna lumen 70 and extends along the length of shaft 32. Formed on the end of coaxial cable 66 is microwave antenna 57, which is surrounded by multi-lobe balloon 58. In an exemplary embodiment, microwave antenna lumen 70 is located eccentric to the longitudinal axis of shaft 32, nearer first side 82 of shaft 32 than second side 84 of shaft 32. In an exemplary embodiment, the center of antenna lumen 70 is offset from the center of shaft 32 towards first side 82 of shaft 32 by 0.007 inches. Alternatively, antenna lumen 70 maybe centered within catheter shaft 32. As shown in FIG. 4B, antenna lumen 70 is sealed at a distal end by plugs 70A and 70B, forming cavity 86 therebetween. At its proximal end, microwave antenna lumen 70 communicates with microwave antenna port 44 of handle 30 (FIG. 2). Microwave antenna 57 is permanently positioned within antenna lumen 70 adjacent distal end 54 of shaft 32 near retention balloon 56, and is held in place by fluoropolymeric or comparable heat-shrink tubing 87. Antenna 57 is positioned within antenna lumen 70 so as to be generally situated adjacent the diseased tissue. of prostate 14 when shaft 32 is properly positioned in urethra 10. Antenna 57 includes wound coils carried at the distal end of coaxial cable 66, which carries microwave energy generated by microwave generating source 38 (FIG. 2). In an exemplary embodiment, microwave antenna 57 is an impedance-matched antenna implemented in the manner generally disclosed in U.S. Pat. No. 5,300,099 entitled GAMMA MATCHED HELICAL DIPOLE MICROWAVE ANTENNA, which is hereby incorporated by reference. It is also preferable for antenna lumen 70 and antenna 57 to have a relatively large radial cross-section, about 0.131 inches in an exemplary embodiment, since a larger antenna radius results in lower transmission line losses and also provides greater column stiffness to facilitate insertion of shaft 32 into urethra 10. More specifically, in the embodiment where microwave antenna lumen 70 is located nearer first side 82 of shaft 32 than second side 84 of shaft 32, the orientation of shaft 32 in urethra 10 must be controlled to achieve the desired preferential heating pattern (with more heating on the side to which the antenna is offset, due to the shorter distance between the antenna and tissue on that side). This embodiment is employed where it is desirable to direct less heat in the portion of the prostate toward the rectum than in other portions of the prostate away from the rectum, due to the potential for thermal damage to the rectum (although in other embodiments, a control system may be employed to circumvent this possibility and prevent thermal damage to the rectum). Thus, the antenna assembly is designed to effectively transmit 100% of the torque applied to handle 30 on to the tip of shaft 32 at distal end 54, through porous heat-shrink tubing 85 bonding coaxial cable 66 to the wall of antenna lumen 70 in a region near handle 30 (not shown) and in a region near antenna 57 (shown in FIG. 4A). In other words, if handle 30 is rotated 20 degrees, the tip of shaft 32 at distal end 54 also rotates 20 degrees. When antenna 57 is energized by microwave generating source 38, antenna 57 emits electromagnetic energy which causes heating of tissue within prostate 14.

In an exemplary embodiment of the thermal therapy catheter of the present invention, a special tip may be used at distal end 54 of catheter shaft 32 as is generally known in the art.

In the vicinity of multi-lobe balloon 58, tube 81 is positioned and secured on the outer surface of shaft 32 at a point where the material of balloon 58 has been attached to shaft 32. Tube 81 is a fluid-free tube with a closed distal end and a proximal end which communicates through the wall of shaft 32 with temperature sensing fiber lumen 72. Tube 81 has a length that approximates the length of multi-lobe balloon 58. Temperature sensing fiber lumen 72, temperature sensing fiber tube 81 and the channel therebetween are sized to permit insertion of temperature sensing fiber 69 to monitor the temperature of tissue surrounding shaft 32 when it is inserted into urethra 10, for interpretation and processing by urethral thermometry unit 39 (FIG. 2).

Balloon inflation lumen 76 extends along the length of catheter shaft 32 and communicates through aperture 88 with the interior of retention balloon 56. Inflation fluid supplied under dynamic pressure through inflation port 40 of handle 30 (FIG. 2) to balloon inflation lumen 76 inflates retention balloon 56 through aperture 88 when catheter 28 is properly positioned in urethra 10, with retention balloon 56 positioned in bladder 12.

Cooling lumen 78 extends along the length of catheter shaft 32, providing a path for the flow of cooling fluid therethrough. Plug 77 is positioned in cooling lumen 78 adjacent to a proximal end of multi-lobe balloon 58 to defame a particular fluid flow path through cooling lumen 78 and multi-lobe balloon 58. The fluid flow path provided according to the present invention is described in more detail below.

Figure 5:
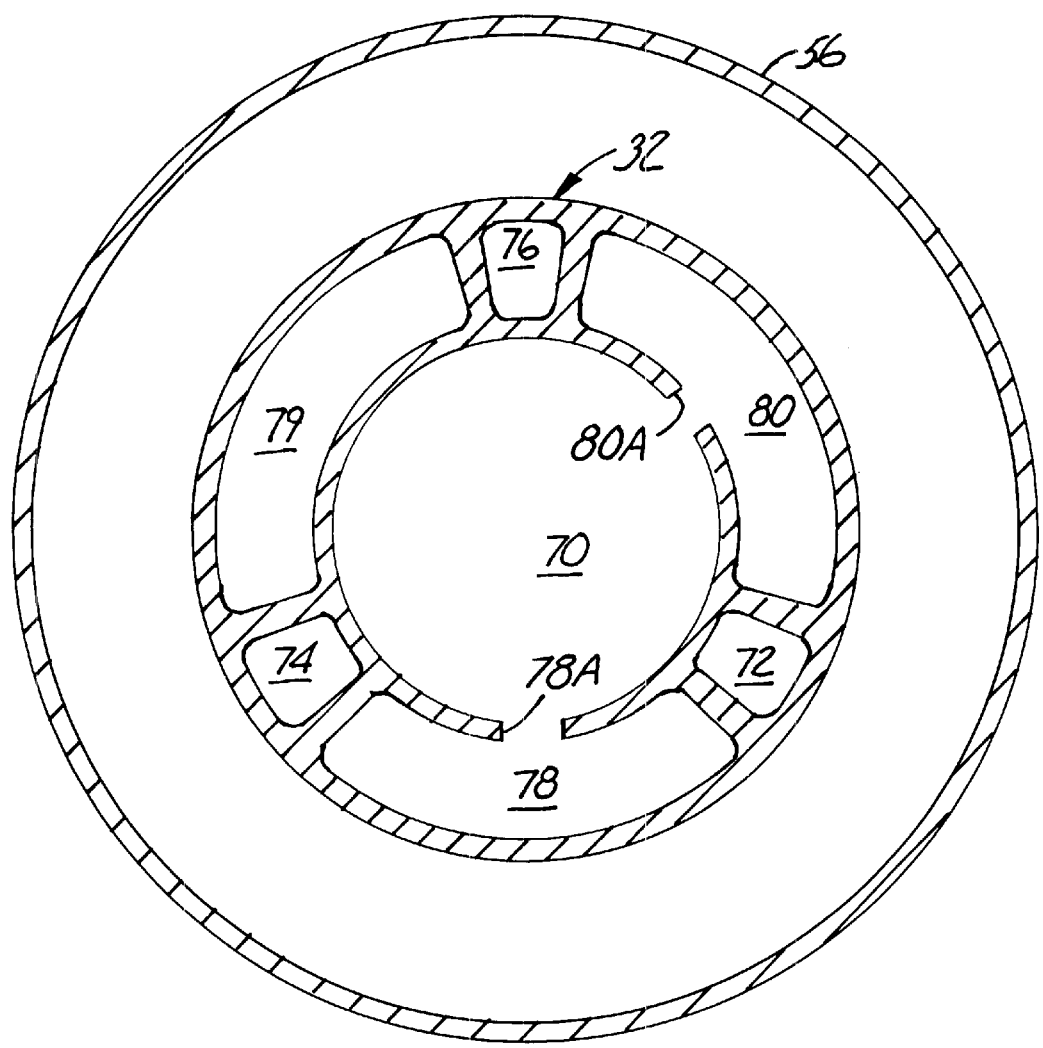
FIG. 5 is a cross-sectional view of the thermal therapy catheter of the present invention, taken along line 5—5 of FIG. 4B.
Figure 7:
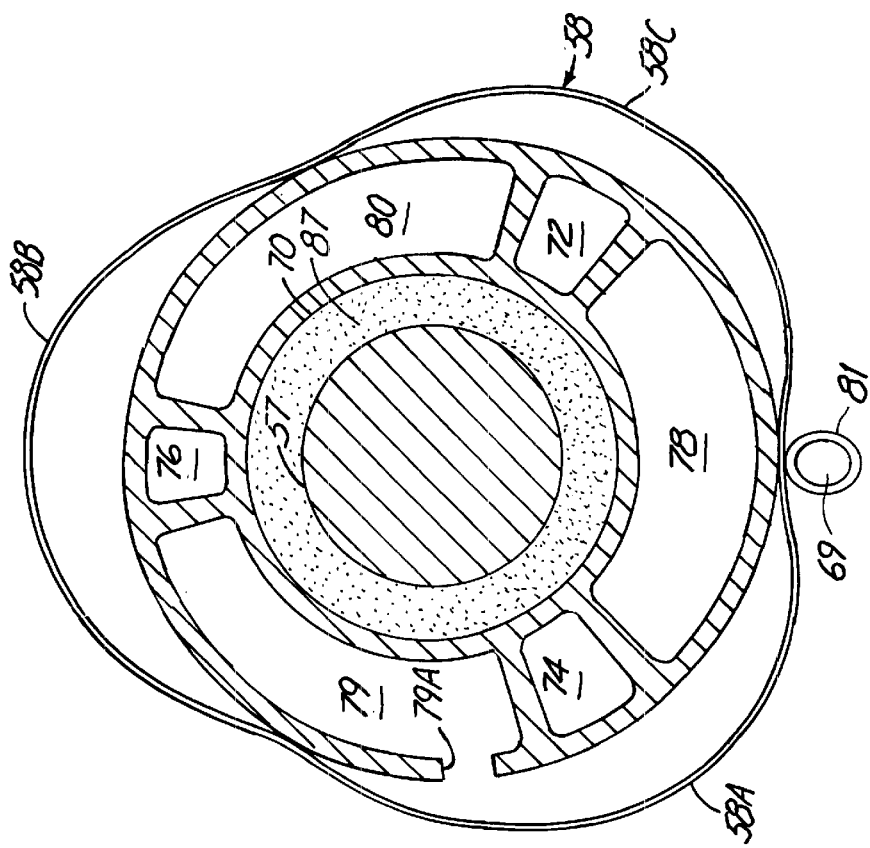
FIG. 7 is a cross-sectional view of the thermal therapy catheter of the present invention, taken along line 7—7 of FIG. 4A.
Figure 6:
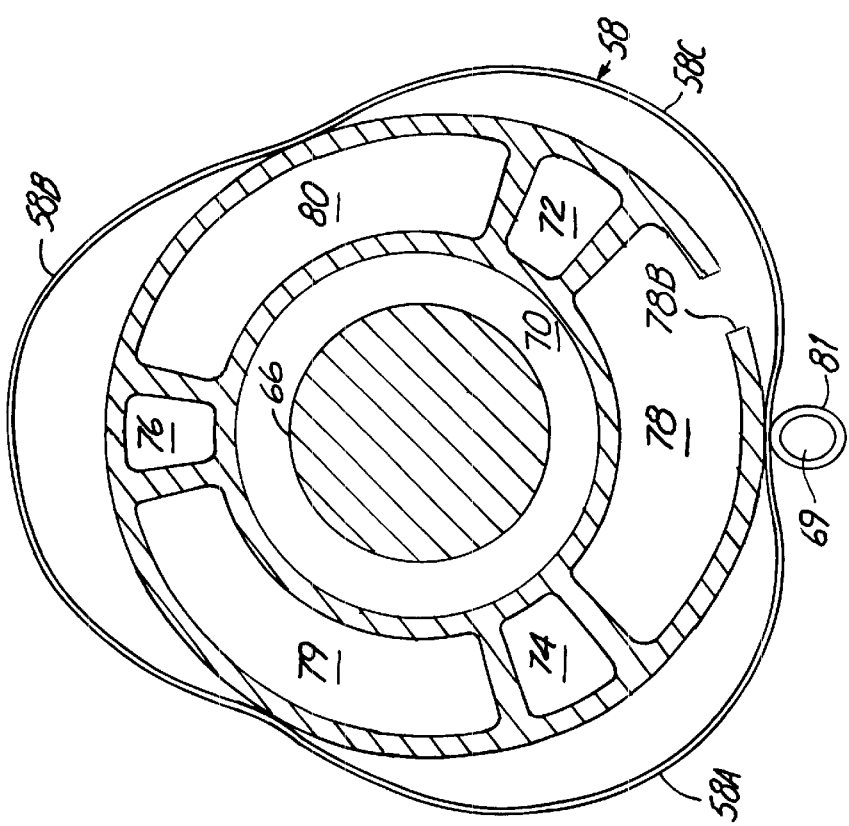
FIG. 6 is a cross-sectional view of the thermal therapy catheter of the present invention, taken along line 6—6 of FIG. 4A.

FIG. 5 is a cross-sectional view of catheter shaft 32 taken along line 5–5 of FIG. 4B, FIG. 6 is a cross-sectional view of catheter shaft 32 taken along line 6–6 of FIG. 4A, and FIG. 7 is a cross-sectional view of catheter shaft 32 taken along line 7–7 of FIG. 4A. While FIGS. 4A and FIG. 4B illustrate multi-lobe balloon 58 in its deflated state, for insertion of catheter 28 into urethra 10, FIGS. 5–7 illustrate multi-lobe balloon 58 in its inflated state, for operating to cool the wall of urethra 10 when microwave antenna 57 is energized.

As shown in FIGS. 5–7, urine drainage lumen 74 is positioned adjacent antenna lumen 70, between antenna lumen 70 and lobe 58A of multi-lobe balloon 58. Urine drainage lumen 74 has a generally trapezoidal cross-section, and together with the catheter walls on either side between cooling lumens 78 and 79 has an included angle of about 30.5 degrees. Urine drainage lumen 74 communicates with urine drainage port 42 of handle 30 (FIG. 2) at proximal end 50 of shaft 32 and with the interior of the bladder at the distal end of catheter shaft 32, and defines a drainage path for urine when catheter shaft 32 is inserted through the urethra into the bladder. Drainage of urine from bladder 12 is necessary due to frequent bladder spasms which occur during transurethral thermal therapy. Again, as mentioned above, in an exemplary embodiment a special tip design maybe used with catheter 28 of the present invention, as is generally known in the art.

Balloon inflation lumen 76 is located adjacent antenna lumen 70, between antenna lumen 70 and lobe 58B of multi-lobe balloon 58. Balloon inflation lumen 76 has a generally trapezoidal cross-section, and together with the catheter walls on either size between cooling lumens 79 and 80 has an included angle of about 29 degrees. Balloon inflation lumen 76 communicates between inflation port 40 of handle 30 (FIG. 2) and the interior of retention balloon to allow for inflation and deflation of balloon 56.

Cooling lumens 78, 79 and 80 are positioned circumjacent to antenna lumen 70, with cooling lumen 78 being located generally between antenna lumen 70 and temperature sensing fiber tube 81 between lobes 58A and 58C of multi-lobe balloon 58, cooling lumen 79 being located generally between antenna lumen 70 and lobes 58A and 58B of multi-lobe balloon 58 and cooling lumen 80 being located generally between antenna lumen 70 and lobes 58B and 58C of multi-lobe balloon 58. Cooling lumens 78, 79 and 80 each have a generally arcuate cross-section, and extend along the length of shaft 32. Cooling lumens 78, 79 and 80 allow for the circulation of fluid around antenna 57 located in antenna lumen 70. Fluid contained within cooling lumens 78, 79 and 80 absorbs a portion of the microwave energy emitted by microwave antenna 57 to control the volume of prostatic tissue in a selected direction that is heated above 45° C. for a time sufficient to necrose the tissue. Fluid within cooling lumens 78, 79 and 80 also absorbs a portion of the heat energy generated by microwave energy from adjacent tissues via thermal conduction. Cooling lumens 78 and 80 include apertures 78A and 80A, respectively, for allowing fluid communication therebetween via cavity 86 in antenna lumen 70. Cooling lumen 78 also includes aperture 78B for allowing fluid communication with lobe 58C of multi-lobe balloon 58, and cooling lumen 79 includes aperture 79A for allowing fluid communication with lobe 58A of multi-lobe balloon 58. In an exemplary embodiment, cooling lumens 78, 79 and 80 each have an included angle of about 90 degrees.

Fluid Flow Path

Cooling lumens 78,79 and 80 cooperate with cooling system 36 via ports 46 and 48 of handle 30 (FIG. 2) to provide a path for selectively controlled flow of fluid through cooling lumens 78, 79 and 80 and through lobes 58A, 58B and 58C of multi-lobe balloon 58 during a treatment session. Cooling lumens 78, 79 and 80 and multi-lobe balloon 58 are designed to provide a serpentine path for the flow of fluid therethrough, providing advantageous cooling performance. Cooling fluid flows from cooling system 36 to cooling fluid feed line 60B and on through port 46 of handle 30 (FIG. 2) into cooling lumen 80, which serves as a fluid intake lumen. The cooling fluid flows under dynamic fluid pressure in cooling lumen 80 toward distal end 54 of shaft 32, and exits cooling lumen 80 through aperture 80A into cavity 86 (created in antenna lumen 70 by plugs 70A and 70B shown in FIG. 4B), as shown in FIG. 5. The fluid flows from cavity 86 through aperture 78A into cooling lumen 78 for flow back toward the proximal end of shaft 32. By creating a path for cooling fluid to flow adjacent to retention balloon 56, the inflation fluid within retention balloon 56 is passively cooled, thereby enhancing patient comfort during treatment. As shown in FIG. 6, the cooling fluid flowing toward proximal end 50 of shaft 32 in cooling lumen 78 exits cooling lumen 78 through aperture 78B into lobe 58C of multi-lobe balloon 58.

Figure 8:
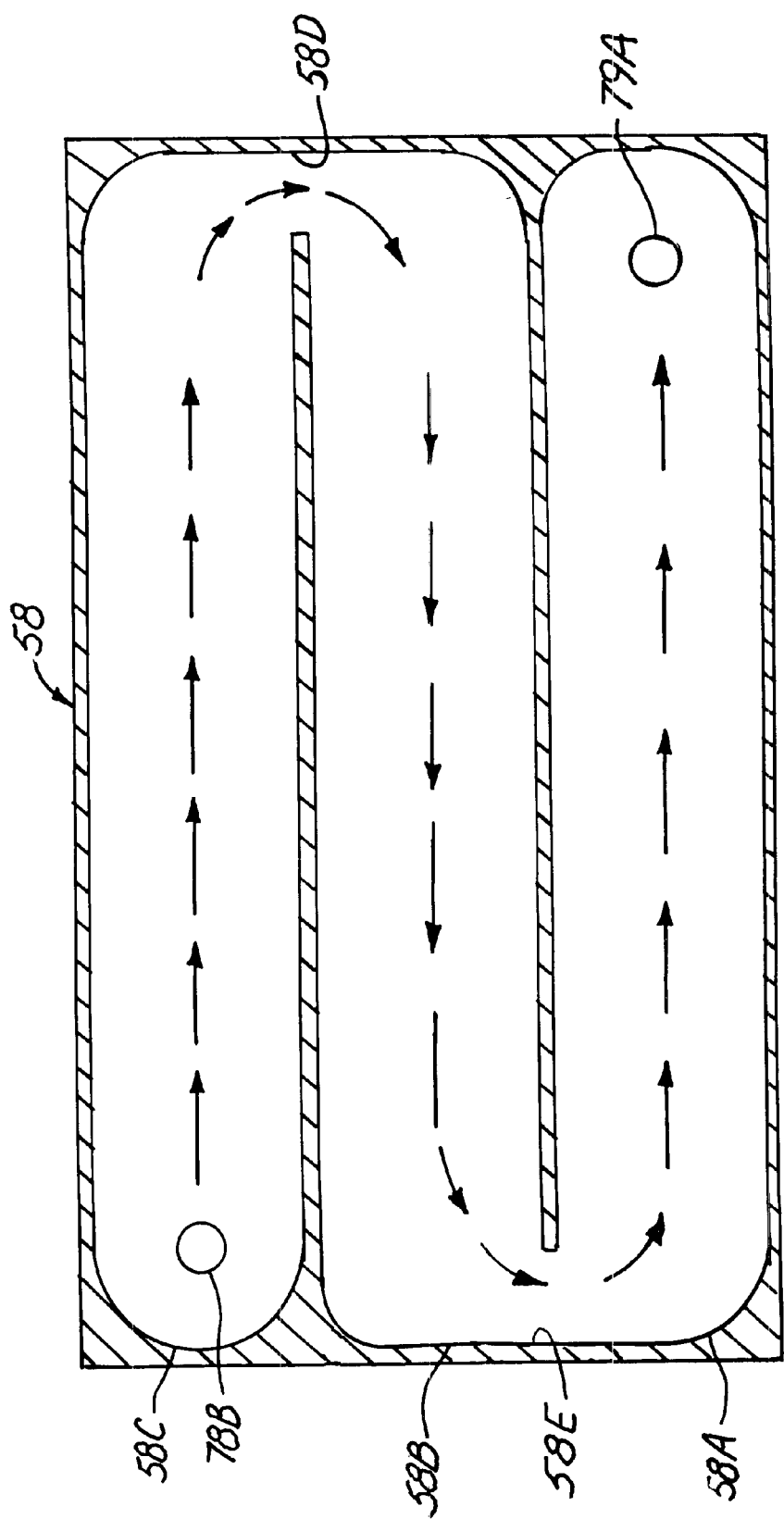
FIG. 8 is a diagram illustrating the flow path of cooling fluid through the multi-lobe balloon of the present invention.

FIG. 8 is a diagram illustrating the pattern of fluid flow through multi-lobe balloon 58. For the purpose of illustration, multi-lobe balloon 58 is shown in FIG. 8 as "flattened out" in two dimensions; it should be understood that multi-lobe balloon 58 is wrapped around catheter shaft 32 in a final assembly of the present invention, as shown in the sectional views of FIGS. 6 and 7. The cross-hatched regions of balloon 58 indicate where balloon 58 is thermally welded (or otherwise attached) to the catheter shaft, with the patterns of multi-lobe balloon 58 being formed by heat stamping or an alternative processing method. Cooling fluid is circulated into lobe 58C of multi-lobe balloon 58 through fluid flow aperture 78B. The cooling fluid flows under dynamic pressure in the serpentine pattern indicated by the arrows in FIG. 8, from lobe 58C through narrow channel 58D to lobe 58B, and through narrow channel 58E to lobe 58A, where the fluid exits through aperture 79A into cooling lumen 79 of catheter shaft 32. Cooling fluid flows through cooling lumen 79, which serves as an exhaust lumen, and exits shaft 32 at proximal end 50 thereof through port 48 of handle 30 (FIG. 2). The overall fluid circulation system described above is operable to circulate cooling fluid throughout cooling lumens 78, 79 and 80 and multi-lobe balloon 58 in a defined fluid flow path, inflating multi-lobe balloon into contact with a wall of the urethra.

The fluid flow path provided by the present invention ensures that the cooling fluid circulates under sufficient dynamic pressure to inflate multi-lobe balloon 58 to a sufficient diameter to provide consistent wall contact with the urethra, such as about 24 French (8 mm) in an exemplary embodiment. In order to achieve a consistent inflated diameter, multi-lobe balloon 58 is formed of a polyurethane film that is blended with photo-initiators and cross-linkers in an exemplary embodiment. With such a cross-linkable film, a maximum inflated diameter may be controlled with a high degree of precision in manufacturing, by inflating multi-lobe balloon 58 with a precise amount of fluid pressure, provided by a precision manufacturing tool, to achieve a repeatable inflated diameter. While multi-lobe balloon 58 is inflated to the desired diameter, the cross-linkable polyurethane film is exposed to ultraviolet (UV) light, setting the maximum diameter of multi-lobe balloon and essentially converting the film of multi-lobe balloon 58 from a distensible material to a non-distensible material having a size corresponding to the desired inflation diameter of multi-lobe balloon 58. As a result, variations in the dynamic pressure of the cooling fluid flowing through multi-lobe balloon will not affect the inflated diameter of the balloon or the force applied by the balloon to the wall of the urethra.

More complex flow patterns in the lobes of balloon 58. are also contemplated by the present invention, which maybe realized by heat stamping and thermal welding processes, or alternatively by adhesive bonding processes, to form the appropriate flow pattern. In addition, multi-lobe balloon 58 maybe formed with more than the three lobes 58A, 58B and 58C illustrated in FIGS. 5–7, thereby modifying the fluid flow pattern and inflation characteristics of balloon 58. The actual amount of dynamic fluid flow pressure may be controlled by adjusting a number of parameters, such as the rate at which cooling fluid is pumped from the cooling system, the width of channels 58D and 58E, the size of fluid flow apertures 80A, 78A, 78B and 79A, the width of restricted flow areas elsewhere in the fluid flow path, and other parameters that will be apparent to one skilled in the art. In an exemplary embodiment, dynamic fluid pressure is controlled by an adjustable restrictor located in the return fluid flow path proximate to cooling system 36.

In an exemplary embodiment, the cooling fluid is deionized or sterile water, chilled to an appropriate temperature so as to maintain the temperature of tissue immediately surrounding catheter shaft 32 at a predetermined value while power is applied to heat diseased prostate tissue. A method of controlling coolant temperature and microwave power to maintain a predetermined tissue temperature is disclosed in U.S. Pat. No. 6,122,551 entitled METHOD OF CONTROLLING THERMAL THERAPY, which is hereby incorporated by reference. The water is pumped at a rate sufficient to provide dynamic pressure to inflate multi-lobe balloon 58 to create an outer balloon diameter of about 24 French (8 mm), with balloon 58 being cross-linked to inflate to this diameter in an exemplary embodiment, thereby ensuring excellent wall contact with the urethra and enhancing the efficiency of the conductive cooling performed by the circulating cooling fluid flowing in multi-lobe balloon 58.

Multi-Port Handle

FIG. 9A is a side view of multi-port handle 30 according to an exemplary embodiment of the present invention. Multi-port handle 30 is a two-piece, molded snap-fit shell, and includes top piece 100 and bottom piece 102 attached together at joint 103 around catheter shaft 32. Inflation port 40, cooling fluid intake port 46 and cooling fluid exit port 48 are formed in top piece 100, and urine drainage port 42 is formed in bottom piece 102.

FIG. 9B is an interior view of top piece 100 of multi-port handle 30, and FIG. 9C is an interior view of bottom piece 102 of multi-port handle 30. FIGS. 9B and 9C are created by folding open top piece 100 and bottom piece 102 of handle 30 at joint 103. Top piece 100 engages with bottom piece 102 in a tongue and groove arrangement, with grooves 104A and 106A in top piece 100 receiving respective tongues 104B and 106B of bottom piece 102. The interior walls of top piece 100 and bottom piece 102 of handle 30 form multiple chambers around catheter shaft 32. Apertures 40A, 46A and 48A are formed in top piece 100 to enable fluid communication between the appropriate lumens of catheter shaft 32 and the respective inflation port 40, cooling fluid intake port 46 and cooling fluid exit port 48. Aperture 42A is formed in bottom piece 102 to enable fluid communication between the urine drainage lumen of catheter shaft 32 and urine drainage port 42. The chambers within handle 30 are sealed from one another by injecting glue in barrier chambers 110 through glue intake apertures 111. Pressure release apertures 112 are formed opposite glue intake apertures 111 to provide an escape path for air in barrier chambers 110 when glue is injected therein.

Variable Pitch Antenna Windings

FIG.10 is a diagram illustrating an embodiment of catheter 28 where antenna 57 is configured with windings having regions of variable pitch, in order to achieve a more uniform pattern of energy emission therefrom. In particular, the metal windings wound around coaxial cable 66 are spaced closer to one another in distal region 122 nearest distal end 123 of antenna 57 than in proximal region 120 nearest proximal end 121 of antenna 74. In other words, antenna 57 has a larger pitch in proximal region 120 than in distal region 122. Preferably, the windings in distal region 122 of antenna 57 have a first pitch and the windings in proximal region 120 of antenna 57 have a second pitch, which is larger than the first pitch of the windings in distal region 122. With respect to catheter shaft 32 shown in FIGS. 4A and 4B, proximal end 121 of antenna 57 is located approximately adjacent to a proximal end of multi-lobe balloon 58 (with a predetermined spacing from the proximal end of antenna 57), spaced from distally located retention balloon 56, while distal end 123 of antenna 57 is located adjacent to a distal end of multi-lobe balloon 58 adjacent to distally located retention balloon 56. The pitch of the windings and the number of windings shown in FIG. 10 are illustrative only (and in fact are quite exaggerated), and are not intended to be shown to scale; in an exemplary embodiment, the spacing of adjacent windings of antenna 57 may be 0.101 inches in proximal region 120 and 0.084 inches in distal region 122

FIG. 11 is a graph illustrating the energy emission field achieved by the variable pitch of the windings of antenna 57 shown in FIG. 10. Curve 130 represents the energy emission field produced by antenna 57, with the vertical axis of the graph representing the energy emitted and the horizontal axis of the graph representing the distance from the tip of the catheter. With the pitch of the windings of antenna 57 varied, and with proper adjustment of other parameters such as the matching capacitance, tap point, and number of turns of antenna 57, an energy emission characteristic (represented by curve 130) maybe created such that peaks 132 are substantially symmetrical and equal, while the slope of curve portion 134 is very steep and rapidly falls to zero, indicating that "back heating" (energy emitted along the length of the catheter further back from antenna 57) does not occur. This is a very desirable energy emission pattern, achieving symmetrical and focused energy emission in the region of antenna 57.

Summary

The present invention provides an improved thermal therapy catheter designed to enhance the efficiency of treatment of diseased tissue from an adjacent body lumen, particularly for treatment of diseased prostate tissue from a urethrally inserted applicator. A multi-lobe balloon is attached around the catheter shaft, with interiors of the balloon lobes in communication with cooling lumens of the catheter, so that circulation of fluid in the cooling lumens dynamically inflates the balloon lobes. As a result, the balloon lobes come into full contact with the wall of the urethra, and the cooling fluid circulating in the balloon lobes is thereby able to efficiently conduct heat away from the urethral wall tissue to preserve the urethra while delivering microwave energy to heat prostate tissue to high temperatures (above about 45° C.) for a sufficient time to necrose the targeted prostate tissue. Implementing a multi-lobe cooling balloon around the catheter shaft provides a very small wall thickness between the actual cooling fluid and the urethral wall, further enhancing the effects of cooling. In one embodiment, the balloon wall thickness is about 0.002 inches. In addition, a cross-linked material is utilized in an exemplary embodiment of the invention so that the multi-lobe balloon is made substantially non-distensible and a repeatable inflated diameter may be achieved in the multi-lobe balloon, with an inflated diameter of about 24 French in one embodiment.

The arrangement and shape of the lumens in the catheter shaft is also designed for efficient operation of the thermal therapy catheter system. As shown in FIGS. 5–7, temperature sensing fiber lumen 72, urine drainage lumen 74 and balloon inflation lumen 76 are all formed with generally trapezoidal cross-sections, so as to minimize the included angle of each of these lumens. As a result, the included angle of cooling lumens 78, 79 and 80 is maximized, improving the efficiency of urethral cooling. In addition, lobes 58A, 58B and 58C of multi-lobe balloon 58 are formed with three seams between the respective lobes. Therefore, there is a potential for "hot spots" in the urethral wall at these seams. To allay this potential difficulty, cooling lumens 78, 79 and 80 are specifically designed so as to be located adjacent to those seams, thereby providing sufficient cooling of the urethral wall at the seams of multi-lobe balloon 58 in addition to the inflated lobes of the balloon. Cooling lumens 78, 79 and 80 also extend along the entire length of the microwave antenna to provide internal cooling of the catheter and thereby ensure that the thermoplastic material of the catheter shaft is not affected by the resistive heating produced by the antenna and the heating produced by absorption of microwave energy by the catheter walls. Furthermore, the fluid flow path of the present invention provides that cooling fluid is flowing in at least one cooling lumen (such as in cooling lumens 78 and 80) adjacent to retention balloon 56 to cool the fluid in retention balloon 56, and also in all of cooling lumens 78, 79 and 80 adjacent to microwave antenna 57, to ensure that the cooling fluid is able to have its maximum cooling effect on the catheter walls adjacent to microwave antenna 57. The presence of fluoropolymeric heat-shrink tubing around the antenna also provides a standoff for spacing the antenna from the wall of the antenna lumen, further reducing the effects of resistive heating on the catheter walls.

Temperature sensing fiber 69 within temperature sensing fiber tube 81 is also strategically placed in the catheter design of the present invention. Temperature sensing fiber tube 81 is located in the seam between lobes 58A and 58C of multi-lobe balloon 58, so as to minimize its effect on the outer perimeter shape of the catheter. In addition, the location of temperature sensing fiber tube 81 also ensures that cooling lumen 78 is positioned directly between temperature sensing fiber 69 and the microwave antenna positioned in antenna lumen 70. As a result, the resistive heating produced by the microwave antenna has no appreciable effect on the temperature reading obtained by temperature sensing fiber 69; the only variables that affect the temperature reading are the actual temperature of tissue immediately adjacent temperature sensing fiber tube 81 and the temperature of the cooling fluid circulating through cooling lumen 78. The cooling fluid temperature may be compensated for by the thermometry unit to yield an accurate value for the actual tissue temperature, which is useful information for controlling the thermal therapy procedure.

The handle design of the present invention is readily manufacturable and is easy to assemble, with chambers in the interior of the handle being definable by injection of glue in an exemplary embodiment. The handle is a two-piece, molded snap-fit shell according to an exemplary embodiment of the invention.

The antenna windings utilized with the catheter of the present invention may have a variable pitch in one embodiment of the invention. For example, the pitch of the windings may be varied to achieve a desired energy-emission characteristic upon energization of the antenna in the catheter.

As a result of the catheter design of the present invention and the efficient cooling of the body lumen wall provided by the invention, a substantial depth of tissue maybe heated above about 45° C. for a time sufficient to necrose the tissue, while protecting the body lumen wall from thermal damage. Under the regulation of an effective control algorithm, such as is disclosed in the aforementioned U.S. application Ser. No. 09/210,033, which has been incorporated herein by reference, the catheter design of the present invention is able to necrose substantially the entire prostate while protecting healthy tissues such as the urethral wall and the rectum, with a treatment time of approximately 30 minutes or less and no need for anesthesia. The present invention therefore offers an extremely attractive therapy option for treating tissue disease such as BPH, with excellent long-term results and a low risk of morbidity or other side effects.

It should be understood that while the present invention has been described with respect to selected embodiments, minor modifications may be made to certain details of the catheter designs shown while still practicing the principles and teachings of the present invention. For example, while specific lumen shapes and sizes have been disclosed, other shapes and sizes are contemplated by the present invention, while practicing the teachings of the invention relating to the motivation for relative lumen positioning and the like.

Although the present invention has been described with reference to preferred embodiments, workers skilled in the art will recognize that changes may be made in form and detail without departing from the spirit and scope of the invention.

What is claimed is:

1. A device for treating tissue adjacent to a body lumen, the device comprising:
   a catheter shaft insertable into the body lumen;
   an energy-emitting element carried by the catheter shaft;
   a multi-lobe balloon around the catheter shaft adjacent to the energy-emitting element, opposing ends of the multi-lobe balloon being sealingly connected to the catheter shaft to form a chamber between the multi-lobe balloon and the catheter shaft; and
   a cooling fluid circulation system for circulating a cooling fluid in the catheter shaft and the chamber in a defined fluid flow path to inflate the multi-lobe balloon into contact with a wall of the body lumen.

2. The device of claim 1, wherein the multi-lobe balloon is substantially non-distensible and is inflatable to a predetermined inflated diameter.

3. The device of claim 2, wherein the multi-lobe balloon is composed of a cross-linkable polyurethane film, and wherein the predetermined inflated diameter is set by inflating the multi-lobe balloon to the predetermined inflated diameter and exposing the cross-linkable polyurethane film while the multi-lobe balloon is inflated to the predetermined inflated diameter.

4. The device of claim 1, wherein the cooling fluid circulation system comprises:
   a plurality of cooling lumens in the catheter shaft, at least one of the plurality of cooling lumens being in fluid communication with at least one lobe of the multi-lobe balloon; and
   a cooling system providing fluid to the cooling lumens and receiving fluid from the cooling lurmens.

5. The device of claim 4, wherein the multi-lobe balloon comprises three lobes around the outer surface of the catheter shaft and the cooling fluid circulation system comprises three cooling lumens.

6. The device of claim 5, wherein a first cooling lumen is located adjacent a first seam between a first lobe and a second lobe of the multi-lobe balloon, a second cooling lumen is located adjacent a second seam between the first lobe and a third lobe of the multi-lobe balloon, and a third cooling lumen is located adjacent a third seam between the second lobe and the third lobe of the multi-lobe balloon.

7. The device of claim 6, wherein the first cooling lumen includes a first fluid flow aperture for communicating fluid with an interior cavity in the catheter shaft, the second cooling lumen includes a second fluid flow aperture for communicating fluid with the interior cavity in the catheter shaft and a third fluid flow aperture for communicating fluid with the first lobe of the multi-lobe balloon, and the third cooling lumen includes a fourth fluid flow aperture for communicating fluid with the third lobe of the multi-lobe balloon.

8. The device of claim 1, further comprising:
   a temperature sensor fiber lumen in the catheter shaft;
   a temperature sensor fiber tube attached to the outer surface of the catheter shaft between lobes of the multi-lobe balloon;
   a channel in the catheter shaft connecting the temperature sensor fiber lumen and the temperature sensor fiber tube; and
   a temperature sensor fiber extending through the temperature sensor fiber lumen, the channel and the temperature sensor fiber tube to sense a temperature of tissue immediately adjacent to the temperature sensor fiber tube.

9. The device of claim 1, wherein the catheter shaft is insertable into a urethra for treating diseased prostate tissue adjacent the urethra.

10. The device of claim 1, further comprising:
    a urine drainage lumen in the catheter shaft.

11. The device of claim 1, further comprising:
    a balloon inflation lumen in the catheter shaft; and
    a retention balloon at an end of the catheter shaft, the retention balloon being in fluid communication with the balloon inflation lumen so as to be inflatable in a bladder to secure the catheter shaft in place in the urethra.

12. The device of claim 1, further comprising a handle connected to a distal end of the catheter shaft, the handle comprising:

a first piece having at least one tongue thereon; and a second piece having at least one groove for receiving the at least one tongue of the first piece, wherein the first and second pieces when assembled form an interior cavity for receiving the catheter shaft therein.

13. The device of claim 12, wherein the handle further comprises a plurality of ports for fluid communication with interior lumens of the catheter shaft, each of the plurality of ports comprising:

a fluid communication chamber in the handle;

an aperture in the handle at the fluid communication chamber for fluid communication with a particular interior lumen of the catheter shaft; and a barrier chamber adjacent to the fluid communication chamber for sealing the fluid communication chamber from other interior regions of the handle.

14. The device of claim 13, wherein the barrier chamber of each of the plurality of ports comprises:

a glue injection aperture for receiving glue to seal the fluid communication chamber from other interior regions of the handle; and a pressure release aperture providing an escape path for air in the barrier chamber when glue is injected therein.

15. The device of claim 1, wherein the energy-emitting element comprises a microwave antenna having a plurality of windings.

16. The device of claim 15, wherein the windings of the microwave antenna have a pitch that is varied along a length of the microwave antenna.

17. A device for treating tissue adjacent to a body lumen, the device comprising:

a catheter shaft having an outer surface, the catheter shaft being insertable into the body lumen;

an energy-emitting element carried by the catheter shaft;

a multi-lobe balloon around the outer surface of the catheter shaft adjacent the energy-emitting element, opposing ends of the multi-lobe balloon being sealingly connected to the catheter shaft to form a chamber between the multi-lobe balloon and the outer surface of the catheter shaft; and a plurality of cooling lumens in the catheter shaft for circulating cooling fluid through the catheter shaft and the multi-lobe balloon, the plurality of cooling lumens being configured for the flow of cooling fluid adjacent to a retention balloon in at least one of the cooling lumens and for the flow of cooling fluid adjacent to the energy-emitting element in all of the cooling lumens.

18. The device of claim 17, wherein the multi-lobe balloon comprises three lobes around the outer surface of the catheter shaft and the plurality of cooling lumens comprises three cooling lumens in the catheter shaft.

19. The device of claim 18, wherein a first cooling lumen is located adjacent a first seam between a first lobe and a second lobe of the multi-lobe balloon, a second cooling lumen is located adjacent a second seam between the first lobe and a third lobe of the multi-lobe balloon, and a third cooling lumen is located adjacent a third seam between the second lobe and the third lobe of the multi-lobe balloon.

20. The device of claim 19, wherein the first cooling lumen includes a first fluid flow aperture for communicating fluid with an interior cavity in the catheter shaft, the second cooling lumen includes a second fluid flow aperture for communicating fluid with the interior cavity in the catheter shaft and a third fluid flow aperture for communicating fluid with the first lobe of the multi-lobe balloon, and the third cooling lumen includes a fourth fluid flow aperture for communicating fluid with the third lobe of the multi-lobe balloon.

* * * * *